United States Patent [19]
Galask et al.

[11] Patent Number: 5,888,523
[45] Date of Patent: Mar. 30, 1999

[54] TOPICAL NON-STEROIDAL ANTI-INFLAMMATORY DRUG COMPOSITION

[75] Inventors: Rudolph P. Galask, Iowa City; Vijay Kumar, Coralville; Gilbert S. Banker, Iowa City, all of Iowa

[73] Assignee: Biocontrol, Inc., Iowa City, Iowa

[21] Appl. No.: 934,948

[22] Filed: Sep. 22, 1997

[51] Int. Cl.$^6$ .............................. A61K 6/00; A61K 7/00; A61F 13/00
[52] U.S. Cl. ........................................... 424/401; 424/434
[58] Field of Search ..................................... 424/434, 401, 424/488, 430; 514/828, 886, 887, 947, 967

[56] References Cited

U.S. PATENT DOCUMENTS

| | | | |
|---|---|---|---|
| 4,985,459 | 1/1991 | Sunshine et al. | 514/561 |
| 5,332,576 | 7/1994 | Juan Mantelle | 424/443 |
| 5,665,364 | 9/1997 | McAtee et al. | 424/401 |

OTHER PUBLICATIONS

Nov. 5, 1983 pp. 609–612 vol. 6 Obstetrics and Gynecology, Woodruff and Parmley, "Infection of the Minor Vestibular Gland".

Feb. 1987 pp. 110–114 vol. 32 The Journal of Reproductive Medicine, Eduard G. Friedrich, Jr., M.D., LLD., "Vulvar Vestibulitis".

Jun. 1991 pp. 1609–1616 vol. 164 AM J Obstet Gynecol, Martha F. Goetsch, M.D., "Vulvar Vestibulitis, Prevalence and Historic Features In A General Gynecologic Practice Population".

*Primary Examiner*—Thurman K. Page
*Assistant Examiner*—Sharon Howard
*Attorney, Agent, or Firm*—Zarley, McKee, Thomte, Voorhees & Sease

[57] ABSTRACT

A means and method for treating inflamed mucosal tissues topically with a non-steroidal anti-inflammatory drug (NSAID) is described. The NSAID is incorporated into a substantive film forming aqueous based carrier system consisting of a water dispersible natural cellulosic polymer and an organic acid. The NSAID composition may further include a water soluble or water hydratable viscosity enhancing agent and/or a plasticizer. The NSAID topical composition is especially effective in treating pain associated with vulvodynia or vulvar vestibulitis.

25 Claims, No Drawings

TOPICAL NON-STEROIDAL ANTI-INFLAMMATORY DRUG COMPOSITION

FIELD OF THE INVENTION

This invention relates to a composition and method for treating patients with mucosal inflammatory disorders, and especially vulvar vestibulitis. Specifically, this invention relates to the topical treatment of erythema and pain of the vulvar vestibule using a nonsteroidal anti-inflammatory drug (NSAID), such as naproxen.

BACKGROUND OF THE INVENTION

The principal organs of the human female reproductive tract include the ovaries, fallopian tubes, uterus, and the vagina. The vagina comprises a musculomembranous tube which forms the passageway between the uterus and the entrance to the vagina between the external vulvae. The vulvae include the labia majora, consisting of two folds of cellular adipose tissue lying on either side of the vaginal opening which form the lateral borders of the vulva. The labia minora lies within the labia majora and encloses the vestibule of the vagina. The vestibule is an almond-shaped space between the lines of attachment of the labia minora. The covering membranes of the vestibule are constructed of delicate, non-keratinized, stratified squamous epithelium.

Vulvar vestibulitis syndrome is an inflammatory process of the vestibule of the vagina which involves the mucous membrane and its underlying appendages, the lesser vestibular ducts and glands. It is characterized by a variety of symptoms, including severe pain on vestibular touch or vaginal entry, tenderness to pressure localized within the vulvar vestibule, and erythema confined to the vestibule.

Vulvar vestibulitis is extremely common. In fact, it has been estimated that approximately 15% of women visiting their gynecologist have vulvodynia or vulvar vestibulitis. Goetsh, M. F., Vulvar vestibulitis: Prevalence and historic features in a general gynecologic practice population: Amer. J. Obstet. & Gynecol., 1991; 164: 1609–1616.

Vulvar pain and its associated problems of dysparunia (pain during sexual intercourse) and vaginismus, or spasm of the leavator muscles, was first described by Skene over one hundred years ago when he wrote about the finding of "excessive sensitivity or hyperesthesia" of the vulva. Skene, A. J. C.; Treatise on Disease of Women, 1889; Apleton and Company, New York. Subsequently, in 1928, Kelly described finding "exquisitely sensitive deep red spots in the mucous of the hymeneal ring" and hypothesized that it could be the source of dysparunia. Kelly, H. A., Gynecology 1928; Apleton and Company, New York. Since that time, vulvar pain and the inability to have intercourse has been called vulvodynia or vaginismus, and was thought to be predominantly a psychological disorder.

Recently, Woodruff and Parmley described a lesion associated with vulvar pain which was erythematous and confined to the vestibule of the vagina and recommended a surgical approach for therapy. Woodruff, J. D. and Parmley, T. H.; Infection of the minor vestibular gland; Obstet. & Gynecol., 1983; 62: 609–612. Later, Freidrich described the lesion in greater detail, named it vulvar vestibulitis syndrome, and concurred that the surgical approach was necessary in most cases. Freidrich, E. G.; Vulvar vestibulitis syndrome: J. Reprod. Med., 1987; 32: 110–114.

Women suffering from vulvar vestibulitis have varying degrees of pain from mild discomfort to severe wherein the woman is unable to walk and/or experiences pain with intercourse. Intercourse in most patients is impossible due to the severity of the pain with insertion and thrusting. Following intercourse, there is usually swelling and pain for several hours to several days. Vulvar vestibulitis can last for years and places a great burden on any relationship the individual may have. Patients with vulvar vestibulitis typically show erythema, occasionally erosion, hypertrophy of the vestibular ducts, and extreme tenderness when the area is touched with a cotton tipped applicator.

The cause of vulvar vestibulitis is uncertain, with yeasts, human papilloma viruses, contact irritants, and other factors being suggested as possible causes. The symptoms vary in their severity, from periods of relative comfort to periods of excruciating pain. These episodes are unpredictable as to their frequency, duration, or severity of pain. Women with vulvar vestibulitis must not only learn how to cope with the chronic nature of this problem, but frequently with a partner who may or may not be understanding when they are unable or unwilling to have sexual intercourse because of pain. Many of these individuals suffer depression and a number of couples, unwilling to deal with the long term nature of this problem, separate, leaving the person with the disease devastated, feeling inadequate, and willing to attempt any therapy that may have some promise of alleviating the pain.

Currently, surgery, laser therapy, and interferon therapy are the treatments most commonly recommended to patients with vulvar vestibulitis. Surgical removal of the vestibule and its underlying structures is appealing to both the physician and the patient, since it offers a quick and decisive approach. However, surgery is a mutilating procedure leaving the area disfigured and scarred and, in most patients, the ameliorative affect is short, with the return of symptoms in many cases in less than twelve months.

Laser therapy or laser surgery is also disadvantageous since it disfigures the skin, causes hyperestesia in many patients, and its effects are commonly of short duration. Topical steroid therapy has had some benefit in these individuals by decreasing the amount of inflammation in the tissues of the vestibule. However, cortical steroid therapy causes atrophy of the skin, especially in the thinner more delicate mucosal areas and, therefore, long-term use is not feasible. Oral analgesic or anti-inflammatory medications, either steroid or non-steroid, have not shown any beneficial effects in these patients. Anti-depressive medication, counseling and behavior modification techniques are helpful, but do not treat the underlying pain. Recently, relaxation exercises have been proposed to relieve the underlying muscle spasm, but again they do not relieve the pain of the vestibule.

There is therefore a need for a treatment for vulvar vestibulitis which is not disfiguring or harmful to the vestibular tissue, yet which is also effective in treating the pain.

It is believed that in a majority of patients, the disease would improve significantly with time by using conservative topical treatment and allowing the normal immune response to control the underlying process. In order to do this effectively, the drug product must control pain without damaging the integument of the vestibule. In addition, the product should be non-irritating, non-staining, hypoallergenic, and user friendly. None of the products currently available, however, control the pain associated with vulvar vestibulitis. There are also problems with the current delivery systems, especially when applied to the vulva.

The three classes of vehicles/delivery systems that are commonly and widely used in topical preparations for vaginal use are ointments, creams, and water soluble polymers or polymer gels. Ointments are derived from either petrolatum hydrocarbon products or animal fats. The animal fat products are exemplified by lanolin or wool fat. Ointments suffer severe disadvantages when utilized for administration to mucosal surfaces, either in the rectum or vagina. First, ointments are occlusive, placing an oleaginous covering over skin or mucosa which prevents or restricts the ability of the underlying tissue to transpire. This results in maceration of the tissue, which is further exacerbated if the tissue is already irritated. In addition, being oily products which become more fluid at body temperature, ointments tend to soften and flow and stain clothing.

Creams or lotions are either oil-in-water or a water-in-oil emulsion systems. The water-in-oil emulsions have some of the same disadvantages as do ointments since they have an oil external phase. Both classes of emulsions, however, of necessity, contain surface-active or emulsifying agents. These materials are irritating to the eye and to mucus membranes. The irritation is compounded if the membranes are already irritated or compromised.

The polymeric gel or water soluble polymeric carrier system is the newest of the three classes of delivery systems, even though it has been available for around fifty years. This type of system is exemplified by the polyethylene glycols. Combinations of the polyethylene glycols, differing in molecular weight, produce semisolid topical carriers ranging in viscosity and consistency. Other soluble polymers, such as hydroxypropylcellulose, hydroxypropylmethylcellulose, poly(acrylic acids), etc., are used to produce gels, which serve as topical vehicles. All of the materials in this class are highly water soluble. However, these products do not adhere well to wet mucosal surfaces and are quickly released from such surfaces by the moisture that is present, or due to vaginal expansion in response to sexual stimulation. Further, these materials often are also irritating to mucosal surfaces based on their high affinity for water and their tendency to dehydrate and overly dry the mucosal surfaces to which they are applied. The patient often experiences a burning sensation following the application of these delivery systems to the mucosal surface.

The present inventors have now discovered that the use of a non-steroidal anti-inflammatory drug (NSAID) incorporated in a novel aqueous based carrier system is effective for treating the pain associated with vulvar vestibulitis without harming the vestibular tissue. The composition is also effective for treating other inflammatory disorders affecting mucosal and non-keratinized epithelial tissues.

Accordingly, it is a primary objective of the present invention to provide a composition and method for treating inflamed human mucosal and epithelial tissues using a non-steroidal anti-inflammatory drug.

It is a further objective of the present invention to provide a composition and method for treating inflamed human mucosal and epithelial tissues which is effective in decreasing the amount of pain associated with the inflammation.

It is a further objective of the present invention to provide a composition and method for treating inflamed human mucosal and epithelial tissues which is not disfiguring or harmful to the tissues.

It is yet a further objective of the present invention to provide a composition and method for treating inflamed human mucosal and epithelial tissues which is oil-free and nonirritating.

It is still a further objective of the present invention to provide a composition and method for treating inflamed human mucosal and epithelial tissues which is easy to use and economical to manufacture.

The method and means of accomplishing each of the above objectives as well as others will become apparent from the detailed description of the invention which follows hereafter.

SUMMARY OF THE INVENTION

The invention describes a method and composition for treating vulvar vestibulitis and other mucosal tissue inflammatory disorders topically with a non-steroidal anti-inflammatory drug, its prodrugs and analogues. The aqueous composition includes a water dispersible natural cellulosic polymer, an organic acid, and a plasticizer. The composition may further include a water soluble or insoluble viscosity agent.

Topical treatment with the NSAID composition decreases the pain associated with the inflammatory disorder without harming the mucosal tissue. Further, the composition does not stain clothing and is nonirritating.

DETAILED DESCRIPTION OF THE PREFERRED EMBODIMENT

The present invention relates to new uses for non-steroidal anti-inflammatory drugs (NSAIDs). Currently, NSAIDs are widely used in the treatment of painful musculoskeletal conditions. According to a recent report, more than 1% of the population of the United States use an NSAID daily.

Studies show that NSAIDs work through the inhibition of the enzyme cyclooxygenase, resulting in decreased formation of precursors or prostaglandins and thromboxanes from arachidonic acid. The resultant decrease in prostaglandin synthesis and activity in various tissues may block pain impulse generation via a peripheral action or possibly inhibit the synthesis or actions of other substances that sensitize pain receptors to mechanical or chemical stimulation.

The present invention is predicated upon the discovery that NSAIDs provide an effective means of treating inflamed mucosal tissues when they are incorporated in a water based cream/lotion base which is maintained at a controlled pH value of between about 3.0 and 6.0, with the preferred pH being from 3.5–4.5.

NSAIDs, in general, are poorly soluble in water. In order to use them topically, they need to be dissolved in an organic solvent, such as alcohol or acetone, or solubilized with a surfactant. Such preparations cause a burning sensation on the skin, especially when applied to vulva or other mucosal surfaces. In addition, both alcohol and acetone are dehydrating solvents which cause the skin to which they are applied to dry and become inflamed.

In contrast, the NSAID topical formulation of the present invention is non-drying and nonirritating to mucosal and epithelial tissue. Moreover, topical application of the NSAID directly to the inflamed tissue bypasses the side effects typically associated with oral administration of NSAIDs, including gastric irritation and intolerance.

Based on their generalized anti-inflammatory effects and thixotropic properties, the NSAID compositions of the present invention may be generally used for the topical treatment of a variety of mucosal disorders, including ophthalmic, nasal, oral, vaginal, and rectal inflammations. Such applications of the NSAID topical composition would be readily appreciated by those skilled in the art using the present disclosed teachings. For example, an ophthalmic composition would have to be manufactured and packaged for sterile administration.

The NSAID carrier of the present invention is natural, oil free, and is formulated with environmentally friendly ingredients. Further, the product is safe, hypoallergenic, non-staining, and non-irritating. The NSAID composition coats the skin or mucosal membrane much like an ointment, but does not macerate or irritate the skin, especially the vulva and other nonkeratinized skin. The resulting film is substantive, and allows the skin to breathe. Further, the NSAID composition does not soak into the skin, so it is not a drying agent such as creams.

Other drugs besides NSAIDs which are compatible with the carrier ingredients may also be incorporated into the NSAID carrier of the present invention. Such drugs may be readily ascertained by those of ordinary skill in the art. These drugs include antibiotics, antiviral, and antifungal agents.

The NSAID carrier system of the present invention is a new colloidal dispersion consisting of a water insoluble yet hydratable and dispersible cellulose material, an organic acid, and, optionally, a plasticizer. Depending on the viscosity of the dispersion, a water soluble or insoluble viscosity enhancing agent may also be included to thicken the composition. As typical examples of NSAIDS, the following compounds can be incorporated in the colloidal carrier system of the present invention:

fenamate derivatives, including meclofenamate and mefenamic acid;
indoleacetic acid derivatives, including indomethacin;
naphthylalkanone derivatives, including nabumetone;
oxicam derivatives, including piroxicam and tenoxicam;
phenylacetic acid derivatives, including diclofenac;
provionic acid derivatives, including fenoprofen, flurbiprofen, ibuprofen, ketoprofen, naproxen, oxaprozin, and tiaprofenic acid;
pyranoindoleacetic acids, including etodolac;
pyrazole derivatives, including phenylbutazone;
pyrroleacetic acid derivatives, including sulindac and tolmetin; and
salicylic acid derivatives, including diflunisal It is understood that the present invention contemplates the use of not only the above-stated NSAID compounds themselves, but their prodrugs which metabolize to the compound and the analogues and biologically active salt forms thereof, as well as optical isomers which provide the same pharmaceutical results.

Generally, even low concentrations of NSAID in the topical carrier will be suitable, requiring only that more frequent topical application be resorted to. As a practical matter, however, to avoid the need for repeated application, it is desirable that the topically applied composition be formulated to typically contain from about 0.5% to about 10% by weight of NSAID. The preferred range of NSAID is from about 3.5–7.5% by weight.

The cellulosic, film-forming material of the instant invention can be from the group consisting of highly purified forms of cellulose described in U.S. Pat. No. 5,414,079, oxidized forms of cellulose disclosed in U.S. Pat. Nos. 5,405,953, and 5,417,984, and a microfibrillated purified cellulosic colloid prepared from a reaction between cellulose and hydrochloric acid, or other appropriate mineral acids, such as phosphoric, sulfuric, or nitric acid, at elevated temperatures. The disclosures of the above-stated patents are herein incorporated by reference. Other cellulosics including those described in Battista et al., U.S. Pat. No. 2,978,446 (1961) can also be used. The highly purified celluloses have controlled reduced levels of crystallinity and controlled molecular weights, whereas the microfibrillated purified cellulose is a readily water dispersible crystalline aggregate.

In comparison, oxidized celluloses are modified celluloses containing aldehyde, carboxylic, and/or ketone functionality (ies) in addition to the hydroxyl groups. These materials all have the ability to produce films through the coalescence of the colloidal particles. They also have the ability to adhere to keratinized and nonkeratinized skins and other surfaces such as glass and metals.

Since cellulose has highly polar hydroxl groups and readily allows water vapor transmission, the resulting films do not produce occlusion, and are not barriers to transpiration of skin or mucosa. Further, cellulose is a neutral and non-reactive polymer, is a building block of the plant kingdom, and is the safest of all polymers known to man. This new carrier system has substantial advantages to topical drug delivery, and especially in delivery of agents to mucosal membranes such as those found in the rectum or vagina.

The cellulosic solid content of the NSAID composition may vary between about 2.5–40.0% by weight, depending on the type of cellulosic colloid and other ingredients present in the preparation. The cellulosic solid in the product containing no viscosity enhancing agent may range between 10–30%, by weight. In compositions that contain a viscosity agent, the cellulose solid may vary between 2.5–<10%, by weight, depending on the amount of viscosity agent present in the product.

The organic acid serves as a component in maintaining the pH of the composition and the vaginal fluid. The organic acid should present the properties of non-irritation and non-burning when applied to the skin. Further, the organic acid should help maintain the normal pH of the mucosal area and not destroy the microflora of the vaginal fluid if applied to the vaginal mucosa. Acceptable organic acids include citric acid, acetic acid, and lactic acid. L-lactic acid is the preferred organic acid since it is one of the constituents of vaginal fluid. Inorganic acids may also be substituted for the organic acid in the composition. However, the inorganic acids are generally more irritating to the mucosal area and are therefore less preferred. The organic acid may be present in a range of between about 0.05–2.0% by weight, with 1% by weight being preferred.

The instant invention may further include a plasticizer to provide flexibility to the films and to prevent flaking. The preferred plasticizers for the NSAID composition include glycerin, polyethylene glycols, propylene glycol, and the like. Other suitable plasticizers include vegetable oil (e.g., corn oil, cottonseed oil, sesame oil, etc.), mineral oil, dialkyl sebacates, dialkyl phthalates, triacetin, and trialkylcitrate. A plasticizer should be added if the area to which the NSAID composition is being applied is not extremely moist. If a plasticizer is included, it should be present in the NSAID composition in an amount ranging from about 1.0–15% by weight, with 5.0–10% by weight being preferred.

The NSAID composition may also contain a water soluble or insoluble viscosity agent to thicken the composition if necessary to help maintain the composition in the area to which it is applied. Generally, if the cellulosic material is added in its upper range, the composition should be thick enough without the addition of a viscosity enhancing agent. The need for a viscosity enhancing agent can be readily ascertained by those of ordinary skill in the art. Water soluble viscosity enhancing agents may include cellulosic polymers, such as methylcellulose, hydroxyethylcellulose, hydroxypropylcellulose, hydroxypropylmethylcellulose, sodium carboxycellulose, and pyrrolidones, and water insoluble materials such as fumed silica, Magnabrite®, and the like.

The preferred viscosity enhancing agent is an acrylic acid polymer, such as Carbopol®. This is used as a Carbopol®/triethanolamine or aqueous base combination since these agents can be used in small amounts to impart the desired viscosity and because it is less supportive of bacterial growth than natural polymers. Since Carbopol® is acidic, triethanolamine is preferably added as a neutralizing agent in conjunction with the Carbopol®. Further, when triethanolamine or a base is added to a formulation containing Carbopol®, it ionizes the Carbopol® resin. As a result, the polymer develops negative charges along the backbone, causing uncoiling of the molecule into an extended structure and, hence, an increase in the viscosity of the solution. The Carbopol® or Carbopol®/triethanolamine combination should be present in the NSAID composition in an amount of from about 0.01–0.75% by weight, and preferably in an amount of between 0.2–0.4% by weight. Other viscosity enhancing agents should be added in an amount of from about 0.1–7.0% or higher, depending on the viscosity of the formula required.

The NSAID carrier system can be readily prepared by mixing appropriate amounts of the ingredients in a high shear mixer. Once thoroughly mixed, it may be necessary to add either triethanolamine or an aqueous solution of a base, such as sodium hydroxide or potassium hydroxide, to adjust the pH values to between 3.0 and 6.0, and preferably between 3.5 and 4.5. It is preferable to pass the resulting cream/lotion product through a colloid mill to ensure homogeneity.

Since the colloidal particles of the present invention provide a carrier with enormous surface area, the particles serve as reservoirs and provide solvency for the NSAID and a number of other classes of drugs. By being able to incorporate drugs in solution phase and at a molecular level of distribution, wholly or in part, in the water-based colloidal carriers of the present invention, the irritancy effects typically seen with NSAIDs and other drugs when deposited on mucosal surfaces or other non-mucosal surfaces are significantly reduced, if not completely eliminated. When there is no crystalline drug present, there are no regions of high drug concentration and, hence, no direct contact of the crystalline drug with the absorbing surface. Regions of high solute concentration, especially for drugs that are basic or acidic moieties, pose serious irritancy effects on mucosal surfaces and especially on those that are inflamed. By having the drug in solution phase in the carrier, direct diffusion of drugs to the tissues is also facilitated. The plasticization of the colloidal particles with an appropriate agent further facilitates permeability of the drug from the carrier to the tissues.

The new colloidal NSAID carrier system, owing to its thixotropic properties, rubs in and spreads smoothly, and provides excellent adhesion to a variety of substrates, including mucosal membranes, such as those found in rectum, vagina, mouth, eyes etc. The films that result on application are substantive. This allows for prolonged contact of the NSAID with the membrane of interest, thereby producing controlled release and long lasting effects. The substantivity of the films resists dislocation due to sweating phenomenon and vaginal expansion in response to sexual stimulation. The nondispersing characteristic of the film causes NSAID to diffuse through the mass, thus providing therapeutic effects for prolonged periods of time.

As set forth above, NSAIDs, in general, are poorly soluble in water. Normally, in order to use them topically, they need to be dissolved in an organic solvent, such as alcohol or acetone, or a surfactant. Such preparations cause a burning sensation on the skin, especially when applied to vulva or other mucosal surfaces. In addition, both alcohol and acetone are dehydrating solvents, causing the skin to dry and become inflamed. The colloidal cream/lotion carrier system of the present invention allows direct incorporation of NSAIDs at a molecular dispersion level, without first dissolving them in an organic solvent or a surfactant. In addition, it exhibits ease of application and lack of irritation to the mucosal membrane.

The new colloidal delivery system, despite being 100% water based, is effective in preventing and inhibiting microbial growth. This is primarily due to the acidity of the composition. This allows the NSAID compositions to be appropriately used on ophthalmic mucosal surfaces, although the composition should be sterilized prior to application if being used ophthalmically. Less than $1 \times 10^2$ CFU/ml growths of $E.$ $coli$ 25922, $S.$ $aureus$ 29213, $P.$ $aeruginosa$ 27853, and $E.$ $faecalis$ were observed with the NSAID composition after 24 and 48 hours. When applied to the vulva, the product of the present invention not only resists attack by vaginal microflora, it maintains the normal vaginal microflora, thus preventing yeast infection.

Topical NSAID preparations can include a variety of substances, including suitable stabilizers, wetting, dissolving, and sweetening agents as well as colorings, moisturizers, preservatives, and fragrances. These minors are added in small amounts and are conventionally known in pharmaceutical formulation work to enhance elegance. Such minors should comprise less than 1% of the overall composition.

Other drugs may also be added to the NSAID composition, so long as it is compatible with the NSAID and the remaining ingredients. These drugs include antibiotics, antiviral, and antifungal agents. Since mucosal inflammatory disorders are often accompanied by infection, a NSAID/antiinfective composition would be a logical combination.

The NSAID composition of the present invention is administered topically in dosages effective to provide the desired treatment enhancement condition. The topical composition of NSAID should comprise from about 0.5 to about 10.0% by weight of the total product. The preferred NSAID concentration is from about 3.5 to about 7.5% by weight of the total product. It can be administered from once a week up to six times per day, with one application every other day being preferred. The patient should apply a thin layer of the composition to the affected area. Typically, a ½ to one inch ribbon of the composition, as squeezed from the product container (tube), is sufficient to coat most inflammations.

The following examples are offered to illustrate but not limit the invention. Thus, they are presented with the understanding that various formulation modifications as well as method of delivery modifications may be made and still be within the spirit of the invention.

EXAMPLE 1

Preparation of NSAID Colloidal Carrier System

The aqueous cellulosic colloid employed in the present invention was prepared according to the procedure described in U.S. Pat. Nos. 5,414,079, 5,405,953, and 5,417,984 (herein incorporated by reference), or from a reaction between cotton linter and 2N hydrochloric acid at 95°–100° C. for a period until the cotton linter fibers were converted into a finely dispersed powder. The resulting powder was filtered, washed extensively with water either by filtration or decantation, to a neutral pH, and then redispersed in water to produce a colloid. The solid content of the cellulose colloids used in the preparation of the product ranged from as low as 7% to as high as 40%, depending on the methods of preparation of cellulosic colloid.

Six hundred milligrams of the acrylic acid polymer (Carbopol®, B.F. Goodrich Company, Ohio) or an appropriate amount of another viscosity enhancing agent was added to a minimum amount of water with stirring. To this stirred solution/dispersion, an appropriate amount of the cellulosic colloid, equivalent to about 10 grams of cellulose solids, 2.0 grams of L-lactic acid, 20 grams of glycerin and water to adjust the total bulk to 100 grams, were added, in this order. The stirring was continued until a homogeneous dispersion was formed. The NSAID colloidal composition was stored in a glass or polyethylene bottle with a screw cap.

EXAMPLE 2

Preparation of 5% Naproxen Topical Cream Product

To a stirred 50 grams dispersion of the NSAID colloidal carrier system, prepared according to the procedure set forth in Example 1, 5 grams of naproxen and 45 grams of water were added. The mixture was stirred using a laboratory-scale mixer or a high shear agitator until a homogeneous dispersion was formed. If the NSAID colloidal carrier contained acrylic acid polymer, than an appropriate amount of triethanolamine or an aqueous solution of a base, was then added dropwise until a pH of 3.5 to 4.0 was reached, and the desired viscosity was obtained. The pH of the dispersion that contained a viscosity enhancing agent other than acrylic acid was adjusted using either a base or an acid. The creamy product thus obtained was stirred for another hour and then homogenized using a hand homogenizer. For large scale preparations, a colloid mill was used. The product was stored in aluminum tubes that had an internal lacquer lining of #15 Gold, #22 Gold, or H-23 Gold.

EXAMPLE 3

To the dispersion of low crystallinity cellulose, oxidized cellulose, or purified cellulose contianing 10–12%, 10–15%, 25–30% cellulose solids, respectively, lactic acid, glycerin, and naproxen in amounts equivalent to 1%, 12%, and 5%, respectively, were added. The mixture was thoroughly mixed using a high shear mixer and then stored in a metal tube that had an internal lining of #15, #22 gold, or H-23 lacquer.

EXAMPLE 4

Preparation of 5% Ibuprofen Topical Cream Product

Except for the change in the drug, the same procedure as described in Example 2 was employed.

EXAMPLE 5

Microbiological Evaluation of NSAID Carrier System

The following five products were prepared according to the procedure described in Examples 1–4:

| | % Composition | | | | |
|---|---|---|---|---|---|
| | I | II | III | IV | IV |
| Cellulose (solid) | 5.0 | 5.0 | 5.0 | 5.0 | 5.0 |
| Carbopol ® 934P | 0.2 | 0.2 | 0.2 | 0.2 | 0.2 |
| Glycerin | 10.0 | — | — | 10 | — |
| Propylene glycol | — | 10 | 10 | — | 10 |
| L-Lactic acid | — | — | 1 | — | — |
| Benzyl alcohol | — | — | — | 1 | 1 |
| Aq. Sodium hydroxide or triethanolamine | a | a | a | a | a |
| Water q.s. | 100.0 | 100.0 | 100.0 | 100.0 | 100.0 | a = added to bring pH equal to 6.0

The sterility of products was tested by innoculating approximately a 0.5 cm column of the product into 5 cc of trypticase soy broth. At 24, 48, and 72 hours a 100 ml sample was spread into a blood agar plate which was then incubated for 24 hours at 35° C. The results indicated all products to be sterile.

EXAMPLE 6

Performance of Naproxen and Ibuprofen Preparations

The performance of the present delivery system and the effect of two different NSAIDs was evaluated in patients suffering from vulvar vestibulitis. Ibuprofen and naproxen were used as model NSAIDs. Twenty-seven subjects were treated with the product containing ibuprofen and fifteen patients with the product containing naproxen.

Each patient was given a tube of the ibuprofen product and a list of questionnaires. Of the twenty-seven individuals who were treated with ibuprofen, twenty-one responded. Twelve out of twenty-one of the individuals who responded, or 57%, included remarks such as:

"I noticed a remarkable decrease of pain within a few days of use, we have even been able to have intercourse for the first time in a year."

"Have felt the most normal that I have felt in years."

"This cream is a miracle, get this cream to the public."

However, nine out of twenty-one of the respondents, or 49%, did not improve or were worse after its use. Four individuals had to discontinue use of the cream because of burning. Burning was noted by 71% of the respondents, or fifteen out of twenty-one of the patients. This was a side effect that was inherent in the ibuprofen rather than the vehicle or the concept, since the control vehicle produced no burning.

In contrast, the patients who were treated with naproxen experienced little to no burning on application. The efficacy was also enhanced significantly. The comments of the patients included:

"I have been a vestibulitis patient for five years and have tried many creams and ointments in hopes of relieving the discomfort of this disease. The latest cream I am using, the 5% naproxen mixture, has provided me with the most relief from my symptoms, and its effects are long lasting."

"The cream works very well, making those difficult days a great deal easier."

"Since I started using the cream I have experienced an improvement in my condition. I found that the cream was easy to apply and did not burn when I applied it. It reduced the redness and irritation of the surrounding skin."

"I was tremendously relieved to finally find a medication that helped my condition."

"The naproxen began to improve my symptoms in just a few days and I noticed continued gradual improvement from the onset. The redness that was present has now taken on a more normal pink look."

"This cream is a miracle as far as I am concerned. Even intercourse is fathomable, the pain is much better and sometimes even minimal."

Based on the performance/effectiveness of the product, it is recommended that the product be used every other day and applied sparingly to the mucous membrane of the vulvar vestibule. Not only did subjects observe and report that every other day use of the product was sufficient to control the symptoms, they also noted that the product provided relief during intercourse, and was not irritating to their partner. When the product is applied subjects usually detect a mild feeling of warmth and the beneficial affects usually occur within thirty minutes. With continued use the mild burning sensation seems to disappear and a decrease in the erythema (redness) is seen. Several individuals have utilized the product for approximately one year and have been able to function in an almost normal lifestyle during that time without loss of efficacy. Given the options of laser ablation, surgical excision, or interferon injections, this treatment modality is not only effective, but significantly less costly, non-mutilating, and non-invasive.

It should be appreciated that the NSAID composition may contain the NSAIDs previously listed, or prodrugs or analogues of these compounds or a racemic mixture of either the D or the L form. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A topical composition for treating mucosal and epithelial inflammatory disorders comprising:
   from about 0.5% to about 10% by weight of a non-steroidal anti-inflammatory in a pharmaceutically acceptable carrier, wherein said carrier further comprises: a water dispersible cellulosic polymer; an organic acid; and water.

2. A composition according to claim 1 wherein the non-steroidal anti-inflammatory drug is from 0.5% to about 10% by weight of the composition.

3. A composition according to claim 1 wherein the pH of the composition is between about 3.0–6.0.

4. A composition according to claim 1 wherein the concentration of cellulosic solid content from the water dispersible cellulosic polymer in the composition is between about 2.5–40.0% by weight.

5. A composition according to claim 1 wherein the composition further includes a water soluble or water hydratable viscosity enhancing agent.

6. A composition according to claim 1 wherein the composition further includes a plasticizer.

7. A composition according to claim 6 wherein the water soluble or water hydratable viscosity enhancing agent is selected from the group consisting of a combination of an acrylic acid polymer and triethanolamine, a water soluble cellulosic polymer, natural gum, fumed silica, pyrrolidine, and magnesium aluminum silicate.

8. A composition according to claim 5 wherein the concentration of the water soluble or water hydratable viscosity enhancing agent in the composition is from about 0.01–10.0% by weight.

9. A composition according to claim 6 wherein the plasticizer is selected from the group consisting of glycerin, polyethylene glycols, propylene glycol, vegetable oil, mineral oil, dialkyl sebacates, dialkyl phthalates, triacetin, and trialkylcitrate.

10. A composition according to claim 6 wherein the concentration of the plasticizer in the composition is from about 1–15% by weight.

11. A composition according to claim 1 wherein the organic acid is selected from the group consisting of citric acid, acetic acid, maleic acid, and lactic acid.

12. A composition according to claim 1 wherein the concentration of the organic acid in the composition is from about 0.05–2.0% by weight.

13. A composition according to claim 1 wherein the non-steroidal anti-inflammatory drug is naproxen.

14. A method of treating mucosal inflammatory disorders comprising:
   topically applying to an affected mucosal area a small but treatment effective amount of a non-steroidal anti-inflammatory drug in a pharmaceutically acceptable carrier.

15. A method according to claim 14 wherein the drug is applied every other day.

16. A method according to claim 14 wherein the pharmaceutically acceptable carrier comprises:
   a water dispersible cellulosic polymer;
   a water soluble or water hydratable viscosity enhancing agent;
   an organic acid;
   a plasticizer; and
   water.

17. A method according to claim 14 wherein the mucosal inflammatory disorder is vulvar vestibulitis.

18. A method of manufacturing a topical non-steroidal anti-inflammatory composition comprising:
   mixing together a water dispersible cellulosic polymer, an organic acid, and water to form a composition; and
   adjusting the pH of the composition to a range of between about 3.0 and 6.0.

19. A method according to claim 18 wherein the mixing step is performed in a high shear mixer or using a conventional laboratory mixer.

20. A method according to claim 18 further comprising the step of:
   passing the composition through a colloid mill.

21. A method according to claim 20 further comprising the step of:
   mixing in a water soluble or water hydratable viscosity enhancing agent and a plasticizer with the water dispersible cellulosic polymer, organic acid, and water.

22. A method of treating mucosal and epithelial inflammatory disorders comprising:

topically applying to an affected mucosal area a small but treatment effective amount of a non-steroidal anti-inflammatory drug, its prodrugs and optical isomers thereof, selected from the group consisting of fenamate derivatives, indoleacetic acid derivatives, naphthylalkanone derivatives, oxicam derivatives, phenylacetic acid derivatives, propionic acid derivatives, pyranoindoleacetic acids, pyrazole derivatives, pyrroleacetic acid derivatives, and salicylic acid derivatives;

wherein the drug is in a pharmaceutically acceptable carrier.

23. A method according to claim 22 wherein the drug is naproxen.

24. A method according to claim 22 wherein the pharmaceutically acceptable carrier comprises:

a water dispersible cellulosic polymer;

a water soluble or water hydratable viscosity enhancing agent;

an organic acid;

a plasticizer; and water.

25. A composition according to claim 1 wherein the cellulosic polymer is selected from the group consisting of a highly purified cellulose, a low crystallinity cellulose, a microfibrillated purified cellulose, and an oxidized cellulose containing low levels of COOH group.

* * * * *